United States Patent [19]

Musser

[11] Patent Number: 5,289,003

[45] Date of Patent: Feb. 22, 1994

[54] PROBE FOR THERMOSPRAY MASS SPECTROMETRY

[75] Inventor: Steven M. Musser, Severn, Md.

[73] Assignee: The United States of America as represented by the Secretary of the Department of Health and Human Services, Washington, D.C.

[21] Appl. No.: 890,194

[22] Filed: May 29, 1992

[51] Int. Cl.$^5$ .................... B01D 59/44; H01J 49/00
[52] U.S. Cl. ..................... 250/288; 250/281
[58] Field of Search .................. 250/281, 288, 288 A

[56] References Cited

U.S. PATENT DOCUMENTS

| 4,641,541 | 2/1987 | Sharp | 250/288 |
|---|---|---|---|
| 4,794,252 | 12/1988 | Bateman et al. | 250/282 |
| 4,804,846 | 2/1989 | Hall | 250/288 |
| 4,814,612 | 3/1989 | Vestal et al. | 250/282 |
| 4,882,485 | 11/1989 | Duryea | 250/288 |
| 4,891,515 | 1/1990 | Jones et al. | 250/427 |
| 4,902,891 | 2/1990 | Vestal | 250/288 |
| 4,908,512 | 3/1990 | Caprioli et al. | 250/288 |
| 4,982,097 | 1/1991 | Slivon et al. | 250/288 A |
| 5,030,826 | 7/1991 | Hansen | 250/288 |

OTHER PUBLICATIONS

Marvin Vestal et al, "Thermospray Liquid Chromatograph/Mass Spectrometer Interface with Direct Electrical Heating of the Capillary", Anal. Chem., vol. 57, No. 12 (1985), pp. 2373-2378.

Primary Examiner—Bruce C. Anderson
Attorney, Agent, or Firm—Lowe, Price, LeBlanc & Becker

[57] ABSTRACT

A thermospray probe assembly which allows for easy replacement or exchange the central capillary tube without requiring replacement of the entire probe assembly when the capillary tube becomes degraded and/or clogged. The replaceable capillary tube is secured at a tip end to a tip of the outer tubular member of the probe assembly by a set screw. The other end of the replaceable capillary tube is sealingly secured by a compression fitting in an adapter connected to the outer tubular member.

20 Claims, 1 Drawing Sheet

PROBE FOR THERMOSPRAY MASS SPECTROMETRY

TECHNICAL FIELD

The present invention relates to probe assemblies, and more particularly relates to thermospray probe assemblies with replaceable capillary tubes.

BACKGROUND ART

Thermospray is a practical ionization method for interfacing liquid chromatography with mass spectrometry. Since its introduction, a vast number of compounds that would otherwise have been very difficult to analyze using mass spectrometry have been successfully identified and quantified. Thermospray has been particularly useful in the analysis of drugs and metabolites from biological matrices.

One of the drawbacks associated with thermospray is that nonvolatile salts and other nonvolatile materials tend to degrade its performance, ultimately clogging the thermospray probe assembly and destroying it.

Several solutions to this problem have been proposed including the use of replaceable ceramic tips and sonication. Such solutions do not prevent the capillary tubing of thermospray probe assemblies from degrading and clogging. Once the capillary tubes become degraded and clogged, the entire probe assembly has to be replaced.

Since a considerable expense is incurred when the probe has to be replaced, there is a need for a thermospray probe assembly which includes a replaceable capillary tube.

DISCLOSURE OF THE INVENTION

It is according one object of the present invention to provide an interface for liquid chromatography and mass spectrometry.

Another object of the present invention is to provide a thermospray probe assembly.

A further object of the present invention is to provide a thermospray probe assembly which has a replaceable capillary tube.

A still further object of the present invention is to provide a combination of a thermospray probe assembly and a removable capillary tube.

According to these and other objects of the present invention which will become apparent as the description thereof proceeds, the present invention provides a thermospray probe assembly which includes:
an outer tubular housing;
an adapter, the outer tubular member being connected at one end thereof to one end of the adapter;
a capillary tube which extends through the adapter and the outer tubular housing, the capillary tube having a tip end which extends to a tip end of the outer tubular housing;
means for releasibly securing the capillary tube in the adapter; and
means for releasibly securing the tip end of the capillary tube in the tip end of the outer tubular housing.

The present invention also provides for an inprovement over existing thermospray probe assemblies which involves means to releasibly secure a tip end of the capillary tube to a tip end of the outer housing.

The present invention further provides for the combination of a thermospray probe assembly and a plurality of interchangeable capillary tubes which includes:
an outer tubular housing;
an adapter, the outer tubular member being connected at one end thereof to one end of the adapter;
means for releasibly securing one of the plurality of capillary tubes in the adapter; and
means for releasibly securing a tip end of one of the plurality of capillary tubes in the tip end of the outer tubular housing.

BRIEF DESCRIPTION OF DRAWINGS

The present invention will be described with reference to the attached drawings which are given by way of a non-limiting examples only, in which.

BEST MODE FOR CARRYING OUT THE INVENTION

The present invention is generally directed to an interface between a liquid chromatography column and a mass spectrometer. The interface receives components which have been separated by the chromatography column. The components, e.g., ions, are contained in a liquid eluent which is vaporized as it is passed through the interface. As a result, the interface (referred to hereafter as a thermospray probe or "probe"), provides a vaporized form of the separated components to the mass spectrometer.

The thermospray probe of the present invention includes a capillary tube through which fluids from a chromatography column are transferred to a mass spectrometer. The capillary passes through the end of the probe and extends to the tip of the probe. Along a portion of the capillary, a heating element, e.g., an electrical resistance heating element, is provided which surrounds the capillary tube. The heating element is used to vaporize eluents or carrier fluids which contain components which are to be analyzed by the mass spectrometer.

The portion of the probe which contains the heating element has an outer tubular member. A Teflon tubing is provided in the annular space between the outer tubular member and the capillary tube, having the surrounding heating element. A metal insert, e.g., stainless steel, is fixed to the tip of the outer tubular member. The metal insert receives the tip of the capillary tube and includes means to releasibly secure the tip of the capillary tube.

The end of the outer tubular member which is opposite the tip of the probe is attached to an adapter which provides means to receive and secure the capillary tube therein. That is, one end of the adaptor is attachable to the outer tubular member, for example by a threaded connection. The other end of the adaptor provides means, for example a compressible fitting, which secures the capillary therein. The capillary tube passes through both ends of the adapter.

A particular feature of the probe assemble of the present invention is that the capillary tube can be easily replaced. Known probe assemblies do not allow for replacement of capillary tubes. Rather, the entire probe assembly has to be replaced at a substantial cost. Such replacement is needed when the capillary tubes degrade and/or become clogged over time.

In addition to being able to replace degraded and/or clogged capillary tubes, the present invention allows different types of capillary tubes to be exchanged, as necessary, when different components are to be analyzed. For example, stainless steel, titanium, nickel, special coated or lined, e.g., glass-lined stainless steel, and other types of capillary tubes can be utilized in a single probe assembly. Prior to the present invention, a different probe assembly was required for each type of capillary tube utilized.

Figure 1:
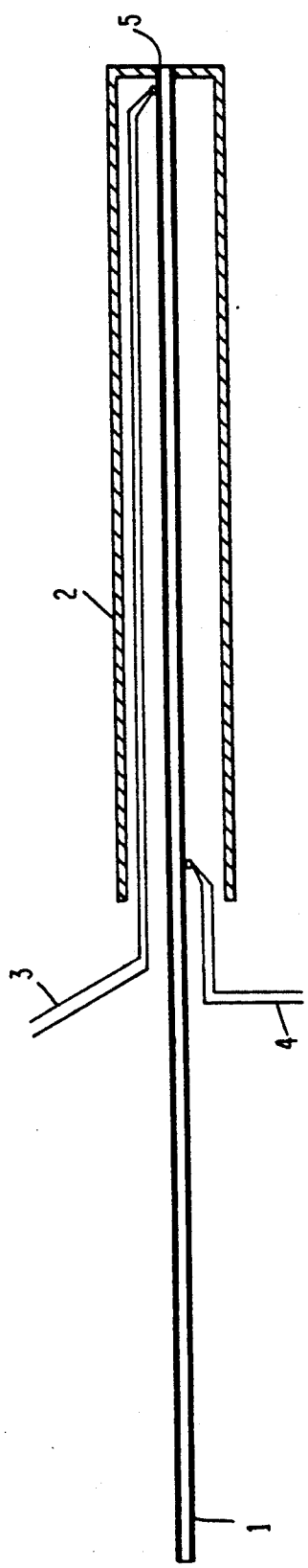
FIG. 1 is a cross-sectional view of a conventional probe assembly.

FIG. 1 is a cross-sectional view of a conventional probe assembly. The probe assembly in FIG. 1 includes a steel capillary tube 1 and an outer tubular member 2 which surrounds one end of the steel capillary tube 2. A tip thermocouple 3 and a control thermocouple 4 are provided to monitor the temperature of the capillary tube 1. The tip of the capillary tube 1 and the outer tubular member 2 are welded together at point 5 as shown. This weld, provides a high vacuum seal between the capillary tube 1 and the outer tubular member 2, and prevents the capillary tube 1 from being removed from the probe assembly.

Figure 2:
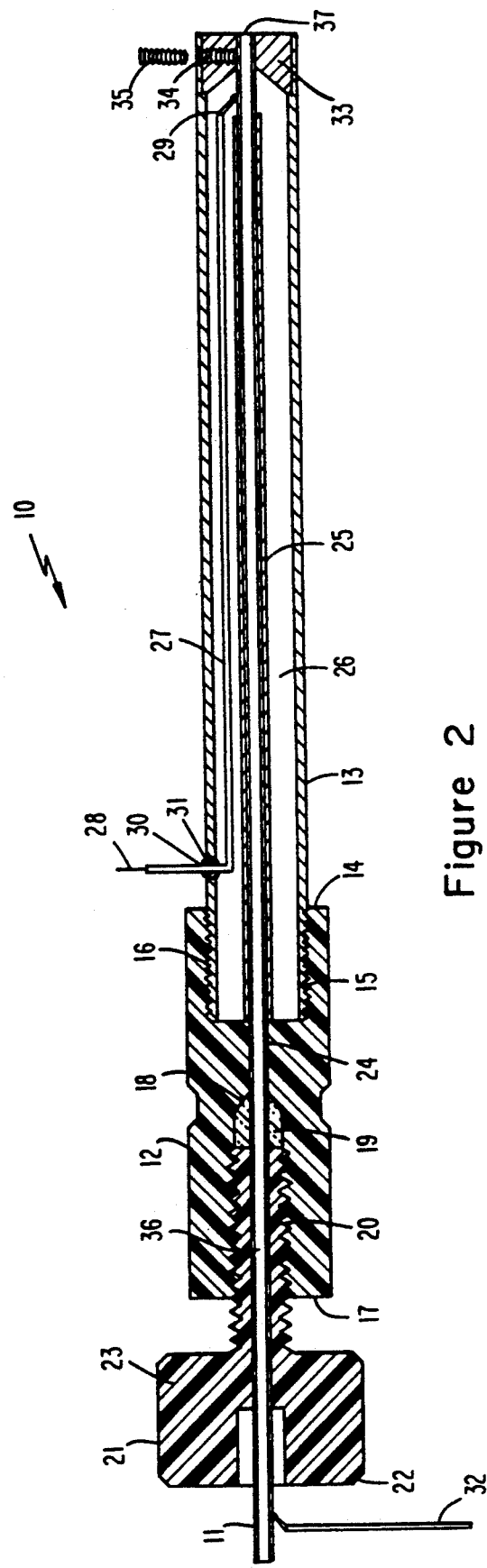
FIG. 2 is a cross-sectional view of a probe assembly according to one embodiment of the present invention.

FIG. 2 is a cross-sectional view of probe assembly according to one embodiment of the present invention. The probe assembly 10 of the present invention includes a capillary tube 11. As shown, the capillary tube 11 passes through an adapter 12 and through an outer tubular member 13. The outer tubular member 13 is connected to one end 14 of the adapter 12 by a suitable connection, such as cooperating threads 15 on the outer tubular member 13 and an internal threaded bore 16 in the adapter 12. The other end 17 of the adapter 12 includes a tapered seat 18 for receiving therein a compressible fitting 19, e.g., ferrule. A threaded bore portion 20 is provided between the tapered seat 18 and the other end 17 of the adapter 12 to receive a nut 21 with complementary threads which can be turned so as to put pressure on the compressible fitting 19. For convenience, nut 21 can have a large head 22 with a gripping surface on an outer circumference 23 thereof. A smooth central bore 24 continues from the tapered seat 18 to the threaded bore 16 at end 14 of the adapter 12.

As shown in FIG. 2, a heating element 25 surrounds the capillary tube 11. According to a preferred embodiment, the heating element 25 is an electrical resistance heating element According to a more preferred embodiment, the capillary tube 11 is used as a heating element. According to this embodiment, an electric current is passed through the capillary tube 11 along its length in a known manner. A heat resistant material is provided between the capillary tube 11 and the outer tubular member 13. In a preferred embodiment, an intermediate tubular member 26 is provided between the capillary tube 11 and the outer tubular member 13. Such intermediate tubular member 26 is preferably made of a heat resistant insulating material such as Teflon and insulates the heating element from the outer tubular member 13.

A small bore 27 is provided in the intermediate tubular member 26 through which the leads 28 of a thermocouple 29 are be fed. The thermocouple 29 is positioned near the tip of the probe assembly, as illustrated, and is utilized to monitor the temperature at the tip of the probe assemble. The leads 28 of the thermocouple pass through the outer tubular member 26 near the adapter 12 through a small hole 30 which is sealed with an epoxy resin 31. Another thermocouple 32 is positioned adjacent the capillary tube 11 upstream of the adapter 12. A temperature comparison between the thermocouples 32 and 29 is used to control the output of the heating element 25 in a known manner.

An insert 33 is provided in the outer tubular member 13 at the tip of the probe assembly. The insert 33 is fixed, e.g., by welding or soldering, to the inside of the outer tubular member 13 and includes a threaded bore 34 in which a set screw 35 can be inserted and tightened against the capillary tube 11.

In use, the capillary tube 11 is inserted through a bore 36 in the nut 21, compression fitting 19, smooth bore 24 of the adapter 12, and the heater element 25 in intermediate tubular member 26. The capillary tube 11 is positioned so that the tip 37 of the capillary tube is substantially flush with the end if the insert member 33. Once the capillary tube 11 is positioned, the set screw 35 is inserted into bore 34 and tightened against the capillary tube member 11. Next, the compression fitting 19 is inserted through bore 20 to tapered seat 18 and nut 21 is tightened in bore 20 to cause the compression fitting 19 to compress around and sealingly secure the capillary tube 11.

When used to introduce components into a mass spectrometer, it is essential that the probe assembly be sealed against the high vacuum of the mass spectrometer. In tests, it has been found that the compressions fitting 19 utilized in the probe assembly of the present invention provides a resealable vacuum seal.

To remove the capillary tube 11, set screw 35 and nut 21 are each withdrawn to release capillary tube 11, which can then be pulled out of the end of the probe assembly. Once removed, a new capillary tube can be inserted and secured in the probe assembly in a reverse manner.

In use, the capillary tube 11 is connected to the outlet of a chromatography column and the tip of the probe assembly if connected to the sample inlet of a mass spectrometer in a known manner.

According to a preferred embodiment, the capillary tube 11 has an outside diameter of 1/16 inches and an inside diameter of 0.005 inches and is made from stainless steel. In this preferred embodiment, the outer tubular member 13 has an outside diameter of ¼ inches and an inner diameter of 5/32 inches and is also made of stainless steel. These and the relative sizes of the other elements of the probe assembly can be easily determined on the basis of flow rates both from the chromatography column and to the mass spectrometer.

Nut 21, compression fitting 19, and adapter 12 are preferably made of a non-corrosive material such as PEEK (polyetherethylketone), Vespel ® (a polyimide from Du Pont), or the like. The other elements of the probe assembly should be made of heat-resistant, non-corrosive materials.

Any type of capillary tube can be utilized in the probe assemble including, stainless steel, nickel, titanium, special coated or lined, e.g., glass-lined stainless steel, etc. The selection of the type of capillary tube is determined on the basis of the inertness of the capillary tube to a particular sample/carrier fluid.

The probe assembly of the present invention is not solely limited for use in conjunction with chromatography columns or mass spectrometers. Discrete samples could be passed through the probe assembly which might be attached to the sample injection port of a mass spectrometer or to the sample injection port of other analyzers, such as a flame photometer.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A thermospray probe which comprises:
   an outer tubular housing;
   an adapter, said outer tubular member being connected at one end thereof to one end of said adapter;
   a capillary tube which extends through said adapter and said outer tubular housing, said capillary tube having a tip end which extends to a tip end of said outer tubular housing;
   means for releasibly securing said capillary tube in said adapter; and
   means for releasibly securing said tip end of said capillary tube in said tip end of said outer tubular housing.

2. A thermospray probe according to claim 1, wherein said means for releasibly securing said capillary tube in said adapter comprises means to provide a vacuum seal between said capillary tube and said adapter.

3. A thermospray probe according to claim 2, wherein said means for releasibly securing said capillary tube in said adapter comprises a compression fitting which surrounds said capillary tube and is positioned in a tapered seat in a bore in said adapter.

4. A thermospray probe according to claim 3, wherein said adapter includes a threaded bore and a threaded nut is provided which is received in said threaded bore for applying pressure to said compression fitting.

5. A thermospray probe according to claim 1, wherein said means for releasibly securing said tip end of said capillary tube in said tip end of said outer tubular housing comprises a set screw which is received in an insert fixed within said tip of said outer housing, said insert having a through bore which receives said tip of said capillary tube.

6. A thermospray probe according to claim 1, wherein said outer tubular member is connecter to said adapter by cooperating threads.

7. A thermospray probe according to claim 1, further including a heating element which surrounds a portion of said capillary tube in said outer housing member.

8. A thermospray probe according to claim 7, further including an intermediate tubular member positioned between said capillary tube and said outer tubular member.

9. A thermospray probe according to claim 8, further including a thermocouple positioned near said tip end of said capillary tube, said thermocouple being within said intermediate tubular member.

10. In a thermospray probe having an outer tubular member and a capillary tube which extends through said outer tubular member, the improvement comprising means to releasibly secure a tip end of said capillary tube to a tip end of said outer housing.

11. A thermospray probe according to claim 10, wherein said means to releasibly secure a tip end of said capillary tube to a tip end of said outer housing comprises a set screw which is received in an insert fixed within said tip of said outer housing, said insert having a through bore which receives said tip of said capillary tube.

12. A thermospray probe according to claim 10, wherein the improvement further comprises an adapter connected to an end of said outer tubular member opposite said tip end thereof, said adapter including means for releasibly securing said capillary tube in said adapter.

13. A thermospray probe according to claim 12, wherein said means for releasibly securing said capillary tube in said adapter comprises means to provide a vacuum seal between said capillary tube and said adapter.

14. A thermospray probe according to claim 13, wherein said means for releasibly securing said capillary tube in said adapter comprises a compression fitting which surrounds said capillary tube and is positioned in a tapered seat in a bore in said adapter.

15. A thermospray probe according to claim 14, wherein said adapter includes a threaded bore and a threaded nut is provided which is received in said threaded bore for applying pressure to said compression fitting.

16. A thermospray probe according to claim 12, wherein said outer tubular member is connecter to said adapter by cooperating threads.

17. The combination of a thermospray probe and a plurality of interchangeable capillary tubes which comprises:
   an outer tubular housing;
   an adapter, said outer tubular member being connected at one end thereof to one end of said adapter;
   means for releasibly securing one of said plurality of capillary tubes in said adapter; and
   means for releasibly securing a tip end of one of said plurality of capillary tubes in said tip end of said outer tubular housing.

18. The combination of a thermospray probe and a plurality of interchangeable capillary tubes according to claim 17, wherein said plurality of capillary tubes are selected from the group consisting of metal capillary tubes and lined or coated capillary tubes.

19. The combination of a thermospray probe and a plurality of interchangeable capillary tubes according to claim 17, wherein said means for releasibly securing said one of said plurality of capillary tubes in said adapter comprises means to provide a vacuum seal between said one of said plurality of capillary tubes and said adapter.

20. The combination of a thermospray probe and a plurality of interchangeable capillary tubes according to claim 17, wherein said means for releasibly securing said tip end of said one of said plurality of capillary tubes in said tip end of said outer tubular housing comprises a set screw which is received in an insert fixed within said tip of said outer housing, said insert having a through bore which receives said tip of said one of said plurality of capillary tubes.

* * * * *

UNITED STATES PATENT AND TRADEMARK OFFICE
CERTIFICATE OF CORRECTION

PATENT NO. : 5,289,003

DATED : February 22, 1994

INVENTOR(S) : Steven M. Musser

It is certified that error appears in the above-identified patent and that said Letters Patent is hereby corrected as shown below:

On the title page, under item [56], before "Other Publications" insert the following:

Foreign Patent Documents

WOA 9,014,686    11/29/90

"Other Publications", line 5, the following should be added:

*ANALYTICAL CHEMISTRY*, Vol. 63, No. 18, September 15, 1991, pages 1989-1998; M.G. Ikonomou et al, "Electrospray-ion spray: a comparison of mechanisms and performance".

*INTERNATIONAL JOURNAL OF MASS SPECTROMETRY AND ION PROCESSES*, Vol. 64, 1985, Amsterdam NL, pages 275-298; P.H. Arpino et al "Design and construction of LC/MS interfaces utilising fused-silica capillary tubes as vacuum nebulizers".

UNITED STATES PATENT AND TRADEMARK OFFICE
CERTIFICATE OF CORRECTION

PATENT NO. : 5,289,003

DATED : February 22, 1994

INVENTOR(S) : Steven M. Musser

It is certified that error appears in the above-identified patent and that said Letters Patent is hereby corrected as shown below:

*JOURNAL OF HIGH RESOLUTION CHROMATOGRAPHY AND CHROMATOGRAPHY COMMUNICATIONS*, Vol. 14, No. 3, March 1991, Heidelberg De Pages 215-216, "A NEW VAPORIZER FOR A THERMOSPRAY LC-MS INTERFACE ON DOUBLE FOCUSING MASS SPECTROMETER".

Signed and Sealed this

Seventh Day of March, 1995

BRUCE LEHMAN

*Attest:*

*Attesting Officer*  *Commissioner of Patents and Trademarks*